(12) United States Patent
Izmirli et al.

(10) Patent No.: US 10,105,107 B2
(45) Date of Patent: Oct. 23, 2018

(54) MEDICAL SYSTEM HAVING COMBINED AND SYNERGIZED DATA OUTPUT FROM MULTIPLE INDEPENDENT INPUTS

(71) Applicant: St. Jude Medical International Holding S.à r.l., Luxembourg (LU)

(72) Inventors: Alon Izmirli, Ganot Hadar (IL); Jeffrey A. Schweitzer, St. Paul, MN (US); Uzi Eichler, Haifa (IL)

(73) Assignee: St. Jude Medical International Holding S.à r.l., Luxembourg (LU)

( * ) Notice: Subject to any disclaimer, the term of this patent is extended or adjusted under 35 U.S.C. 154(b) by 60 days.

(21) Appl. No.: 14/983,529

(22) Filed: Dec. 29, 2015

(65) Prior Publication Data

US 2016/0203608 A1 Jul. 14, 2016

Related U.S. Application Data

(60) Provisional application No. 62/101,133, filed on Jan. 8, 2015.

(51) Int. Cl.
*G06K 9/00* (2006.01)
*A61B 5/00* (2006.01)
(Continued)

(52) U.S. Cl.
CPC .......... *A61B 5/743* (2013.01); *A61B 5/02154* (2013.01); *A61B 5/0402* (2013.01);
(Continued)

(58) Field of Classification Search
CPC ... A61B 5/743; A61B 5/02154; A61B 5/0402; A61B 5/0422; A61B 5/1036;
(Continued)

(56) References Cited

U.S. PATENT DOCUMENTS

| 5,586,201 A | 12/1996 | Whiting et al. |
| 5,822,391 A | 10/1998 | Whiting et al. |

(Continued)

FOREIGN PATENT DOCUMENTS

| WO | 2012176191 A1 | 12/2012 |
| WO | 2014141113 A2 | 9/2014 |

OTHER PUBLICATIONS

"Carto 3 System Fact Sheet", Biosense Webster, 2014, 3 pages.

*Primary Examiner* — Jose Couso
(74) *Attorney, Agent, or Firm* — Dykema Gossett PLLC

(57) ABSTRACT

The present disclosure relates generally to medical systems and methods for combining and synergizing information in an expedient format for viewing on a display screen. In one embodiment, a method for combining and synergizing data from different medical systems comprises obtaining from a first medical system an image disposed relative to a first coordinate system, obtaining from a second medical system supplemental data; synchronizing first and second clocks of the first and second medical systems, respectively, and displaying in synchronicity the supplemental data combined with the image. In other embodiments, coordinate systems of the first and second medical systems can be co-registered. In another embodiment, sensor integration time and spatial accuracy of the first and second medical systems can be used with an algorithm to produce synergized information.

16 Claims, 7 Drawing Sheets

(51) Int. Cl.
*A61B 5/0402* (2006.01)
*A61B 5/103* (2006.01)
*A61B 5/0215* (2006.01)
*G06F 17/30* (2006.01)
*G06F 19/00* (2018.01)
*G16H 10/60* (2018.01)
*H04L 29/08* (2006.01)
*A61B 5/042* (2006.01)
*A61B 5/06* (2006.01)
*A61B 18/14* (2006.01)

(52) U.S. Cl.
CPC ...... *A61B 5/1036* (2013.01); *G06F 17/30557* (2013.01); *G06F 19/321* (2013.01); *G16H 10/60* (2018.01); *A61B 5/0422* (2013.01); *A61B 5/062* (2013.01); *A61B 5/6852* (2013.01); *A61B 5/6885* (2013.01); *A61B 18/1492* (2013.01); *H04L 67/2838* (2013.01); *H04L 67/2895* (2013.01)

(58) Field of Classification Search
CPC ......... A61B 5/062; A61B 5/063; A61B 5/065; A61B 5/6852; A61B 5/6885; A61B 5/7285; A61B 5/7289; A61B 6/463; A61B 6/5247; A61B 6/4417; A61B 6/464; A61B 6/4266; A61B 8/065; A61B 8/08803; A61B 8/463; A61B 8/483; A61B 8/5283; A61B 8/543; A61B 8/4416; A61B 8/464; A61B 8/5261; A61B 18/1492; A61B 34/20; A61B 90/36; A61B 2017/00694; A61B 2034/2051; A61B 2034/2053; A61B 2090/0818; A61B 2090/364; A61B 2090/378; A61B 2090/3925; A61B 2090/3995; G06T 11/60; G06T 19/00; G06T 2207/20212; G06K 2209/057; G06F 3/01; G06F 17/30557; G06F 19/30; G06F 19/3406; G06F 19/321; G06F 19/3418; A61N 5/1048; H04L 67/2838; H04L 67/2895; Y10S 128/916
See application file for complete search history.

(56) References Cited

U.S. PATENT DOCUMENTS

| | | | |
|---|---|---|---|
| 6,148,095 A | 11/2000 | Prause et al. | |
| 6,195,445 B1 | 2/2001 | Dubuisson-Jolly et al. | |
| 6,233,476 B1 | 5/2001 | Strommer | |
| 6,690,963 B2 * | 2/2004 | Ben-Haim | A61N 1/36564 600/117 |
| 6,728,566 B1 | 4/2004 | Subramanyan et al. | |
| 6,731,973 B2 | 5/2004 | Voith | |
| 6,937,696 B1 | 8/2005 | Mostafavi | |
| 6,973,202 B2 | 12/2005 | Mostafavi | |
| 7,134,994 B2 | 11/2006 | Alpert et al. | |
| 7,191,100 B2 | 3/2007 | Mostafavi | |
| 7,263,397 B2 | 8/2007 | Hauck et al. | |
| 7,301,644 B2 | 11/2007 | Knighton et al. | |
| 7,314,446 B2 | 1/2008 | Byrd et al. | |
| 7,321,677 B2 | 1/2008 | Evron et al. | |
| 7,386,339 B2 | 6/2008 | Strommer et al. | |
| RE40,608 E | 12/2008 | Glover et al. | |
| 7,572,223 B2 * | 8/2009 | Donaldson | A61B 8/0833 600/437 |
| 7,593,559 B2 | 9/2009 | Toth et al. | |
| 7,697,972 B2 | 4/2010 | Verard et al. | |
| 7,729,746 B2 | 6/2010 | Redel et al. | |
| 7,742,797 B2 | 6/2010 | Redel | |
| 7,853,316 B2 | 12/2010 | Milner et al. | |
| 7,869,663 B2 | 1/2011 | Buckland et al. | |
| 7,872,759 B2 | 1/2011 | Tearney et al. | |
| 7,918,793 B2 | 4/2011 | Altmann et al. | |
| 7,925,327 B2 | 4/2011 | Weese | |
| 7,930,014 B2 | 4/2011 | Huennekens et al. | |
| 7,967,762 B2 | 6/2011 | Corl et al. | |
| 7,991,105 B2 | 8/2011 | Mielekamp et al. | |
| 8,029,447 B2 | 10/2011 | Kanz et al. | |
| 8,175,076 B2 * | 5/2012 | Pelzek | G04C 13/02 370/350 |
| 8,231,537 B2 | 7/2012 | Ahmed et al. | |
| 8,259,303 B2 | 9/2012 | Johnson et al. | |
| 8,277,386 B2 | 10/2012 | Ahmed et al. | |
| 8,289,284 B2 | 10/2012 | Glynn et al. | |
| 8,290,228 B2 | 10/2012 | Cohen et al. | |
| 8,298,147 B2 | 10/2012 | Huennekens et al. | |
| 8,317,713 B2 | 11/2012 | Davies et al. | |
| 8,351,665 B2 | 1/2013 | Tearney et al. | |
| 8,364,242 B2 * | 1/2013 | Li | A61B 6/541 382/128 |
| 8,406,875 B2 | 3/2013 | Levin et al. | |
| 8,419,647 B2 | 4/2013 | Corl et al. | |
| 8,419,648 B2 | 4/2013 | Corl et al. | |
| 8,457,375 B2 | 6/2013 | Rieber et al. | |
| 8,457,440 B1 | 6/2013 | Johnson | |
| 8,463,007 B2 | 6/2013 | Steinberg et al. | |
| 8,478,384 B2 | 7/2013 | Schmitt et al. | |
| 8,480,593 B2 | 7/2013 | Magnin et al. | |
| 8,491,567 B2 | 7/2013 | Magnin et al. | |
| 8,529,506 B2 | 9/2013 | Brown et al. | |
| 8,531,676 B2 | 9/2013 | Condit et al. | |
| 8,542,900 B2 | 9/2013 | Tolkowsky et al. | |
| 8,556,820 B2 | 10/2013 | Alpert et al. | |
| 8,562,537 B2 | 10/2013 | Alpert et al. | |
| 8,564,783 B2 | 10/2013 | Flanders et al. | |
| 8,568,326 B2 | 10/2013 | Smith | |
| 8,571,639 B2 | 10/2013 | Mostafavi | |
| 8,641,705 B2 | 2/2014 | Leo et al. | |
| 8,670,816 B2 * | 3/2014 | Green | A61B 8/0841 600/407 |
| 8,725,525 B2 * | 5/2014 | Yamaki | G06F 19/327 348/701 |
| 8,811,692 B2 * | 8/2014 | Prokoski | A61B 5/0064 382/128 |
| 8,989,842 B2 * | 3/2015 | Li | A61B 5/06 128/916 |
| 9,092,556 B2 * | 7/2015 | Amble | A61B 5/117 |
| 9,430,614 B2 * | 8/2016 | Dalal | G06F 19/3406 |
| 9,468,413 B2 * | 10/2016 | Hall | A61B 6/12 |
| 9,636,188 B2 * | 5/2017 | Gattani | A61B 90/36 |
| 2005/0080336 A1 * | 4/2005 | Byrd | A61B 8/065 600/428 |
| 2005/0131473 A1 | 6/2005 | Gordon et al. | |
| 2006/0074285 A1 | 4/2006 | Zarkh et al. | |
| 2006/0165270 A1 | 7/2006 | Borgert et al. | |
| 2007/0043292 A1 | 2/2007 | Camus et al. | |
| 2007/0060833 A1 | 3/2007 | Hauck | |
| 2008/0183071 A1 | 7/2008 | Strommer et al. | |
| 2008/0221439 A1 | 9/2008 | Iddan et al. | |
| 2008/0221440 A1 | 9/2008 | Iddan et al. | |
| 2008/0221442 A1 | 9/2008 | Tolkowsky et al. | |
| 2008/0319312 A1 | 12/2008 | Eichler et al. | |
| 2009/0076373 A1 * | 3/2009 | Maschke | A61B 6/032 600/410 |
| 2009/0306547 A1 | 12/2009 | Iddan et al. | |
| 2009/0318003 A1 | 12/2009 | Hossack et al. | |
| 2010/0157041 A1 | 6/2010 | Klaiman et al. | |
| 2010/0160764 A1 | 6/2010 | Steinberg et al. | |
| 2010/0160773 A1 | 6/2010 | Cohen et al. | |
| 2010/0161022 A1 | 6/2010 | Tolkowsky | |
| 2010/0161023 A1 | 6/2010 | Cohen et al. | |
| 2010/0172556 A1 | 7/2010 | Cohen et al. | |
| 2010/0191102 A1 | 7/2010 | Steinberg et al. | |
| 2010/0222671 A1 | 9/2010 | Cohen et al. | |
| 2010/0228076 A1 | 9/2010 | Blank et al. | |
| 2011/0034801 A1 | 2/2011 | Baumgart | |
| 2011/0319752 A1 | 12/2011 | Steinberg et al. | |
| 2012/0004529 A1 | 1/2012 | Tolkowsky et al. | |
| 2012/0004537 A1 | 1/2012 | Tolkowsky et al. | |
| 2012/0029339 A1 | 2/2012 | Cohen et al. | |

(56) References Cited

U.S. PATENT DOCUMENTS

| | | |
|---|---|---|
| 2012/0169712 A1 | 7/2012 | Hill et al. |
| 2012/0230565 A1 | 9/2012 | Steinberg et al. |
| 2012/0265054 A1 | 10/2012 | Olson |
| 2012/0265077 A1 | 10/2012 | Gille et al. |
| 2012/0300215 A1 | 11/2012 | Johnson et al. |
| 2012/0300216 A1 | 11/2012 | Johnson et al. |
| 2012/0302869 A1 | 11/2012 | Koyrakh et al. |
| 2013/0015975 A1 | 1/2013 | Huennekens et al. |
| 2013/0023762 A1 | 1/2013 | Huennekens et al. |
| 2013/0023763 A1 | 1/2013 | Huennekens et al. |
| 2013/0028497 A1 | 1/2013 | Klingensmith et al. |
| 2013/0030295 A1 | 1/2013 | Huennekens et al. |
| 2013/0030300 A1 | 1/2013 | Ahmed et al. |
| 2013/0046167 A1 | 2/2013 | Shah |
| 2013/0046190 A1 | 2/2013 | Davies |
| 2013/0060145 A1 | 3/2013 | Davies et al. |
| 2013/0066193 A1 | 3/2013 | Olson et al. |
| 2013/0120297 A1 | 5/2013 | Merritt et al. |
| 2013/0123577 A1 | 5/2013 | Ho et al. |
| 2013/0123616 A1 | 5/2013 | Merritt et al. |
| 2013/0137981 A1 | 5/2013 | Ho et al. |
| 2013/0137985 A1 | 5/2013 | Ho et al. |
| 2013/0150716 A1 | 6/2013 | Stigall et al. |
| 2013/0178746 A1 | 7/2013 | Ho et al. |
| 2013/0178750 A1 | 7/2013 | Sheehan et al. |
| 2013/0184589 A1 | 7/2013 | Ho et al. |
| 2013/0190633 A1 | 7/2013 | Dorando et al. |
| 2013/0211230 A1* | 8/2013 | Sperling ................. A61B 8/468 600/410 |
| 2013/0289369 A1 | 10/2013 | Margolis |
| 2013/0289391 A1 | 10/2013 | Levy et al. |
| 2013/0317339 A1* | 11/2013 | Waldstreicher .......... A61B 8/12 600/409 |
| 2014/0275851 A1* | 9/2014 | Amble ................. A61B 5/7425 600/301 |
| 2015/0051489 A1* | 2/2015 | Caluser ................ A61B 8/0825 600/440 |
| 2015/0070469 A1* | 3/2015 | Yoshibayashi .......... G06T 19/00 348/46 |
| 2015/0182191 A1* | 7/2015 | Caluser ................ A61B 8/5246 600/440 |
| 2015/0320515 A1* | 11/2015 | Edwards ............ A61B 19/5244 600/389 |
| 2017/0231508 A1* | 8/2017 | Edwards ............ A61B 5/02055 |

* cited by examiner

MEDICAL SYSTEM HAVING COMBINED AND SYNERGIZED DATA OUTPUT FROM MULTIPLE INDEPENDENT INPUTS

CROSS-REFERENCE TO RELATED APPLICATIONS

This application claims the benefit of U.S. provisional application No. 62/101,133, filed Jan. 8, 2015, which is hereby incorporated by reference as though fully set forth herein.

BACKGROUND OF THE INVENTION a. Field of the Invention

The present disclosure relates to medical systems and medical devices employed by medical systems, and more particularly to systems and methods for assimilating information from disparate medical systems and devices.

b. Background Art

Medical systems used in the healthcare industry include various diagnostic, navigation, imaging, mapping, and treatment systems, as well as the various associated medical devices employed by such medical systems.

Medical imaging systems are used to obtain various images, still or moving, of the anatomy of patients. A wide variety of imaging systems are currently available, such as fluoroscopy, angiography, echocardiography, computed tomography, ultrasound, x-ray, nuclear, magnetic resonance imaging (MM) and other imaging systems. Typically, two-dimensional (2D) images are generated with such systems. Often, a real-time, or simulated live, moving image can be generated on a display screen.

Medical mapping systems are used to generate various models or representations of anatomy, such as portions of the heart, with respect to a three-dimensional (3D) reference frame of the mapping system. Common mapping systems and technology include impedance-based systems, such as the EnSite™ Velocity™ system utilizing EnSite™ NavX™ technology, and magnetic- or electromagnetic-based systems, such as the MediGuide™ system, each of which is available from St. Jude Medical, Inc. These systems are capable of generating complex-shaped hulls that can be rotated and viewed from different angles on a display screen.

Medical devices include, for example, ablation catheters, mapping catheters, imaging catheters, pressure and force sensing devices, and many, many others. These devices are typically configured for use with a particular type of medical system. For example, a catheter may have an ablation tip along with location sensors that can place the tip within a 3D model generated by an impedance-based mapping system. Such a catheter typically would not be compatible with a magnetic-based mapping system.

Medical devices are highly complicated and specialized devices due to the complex interaction between living tissue and potentially hazardous technology. For example, many devices have very demanding size constraints for operating within small passages of a body, which additionally increases the cost of the device. Each system and device is, therefore, typically oriented toward obtaining a particular type of data or delivering a specific type of treatment. Thus, each of these systems and devices is typically limited to a small range of procedures, requiring doctors and clinicians to utilize multiple systems and devices to perform additional procedures.

Furthermore, each of these systems may have drawbacks due to the limitations of their particular technology. For example, fluoroscopic images are accurate, but lack depth and soft tissue information, while ultrasound images provide good visualization, but have a limited view plane and include excessive noise. Also, magnetic-based mapping systems may be susceptible to interference from outside objects, while impedance-based mapping systems may be susceptible to "shift and drift" from changes in the physiology (impedance) of the body of the patient.

Information from these various system, however, cannot be combined into a more useful format or presentation. Each of these systems and devices generates data having distinct characterizing parameters, such as data resolution, sampling rate, frequency, accuracy and, the like. Thus, each of these systems typically produces an output that is unique to that system and incompatible with other systems.

Various attempts have been made to combine information from different medical systems. For example, U.S. Pub. No. 2012/0265054 A1 to Olson describes methods for registering multiple navigation systems to a common coordinate frame. U.S. Pub. No. 2012/0302869 A1 to Koyrakh et al. describes methods for correction of shift and drift in impedance-based navigation system using magnetic field information. U.S. Pub. No. 2013/0066193 A1 to Olson et al. describes methods for navigating a catheter using both impedance and magnetic medical systems. U.S. Pat. No. 7,314,446 to Byrd et al. describes methods for time gating medical images. Each of the aforementioned references is hereby incorporated by reference in its entirety for all purposes.

None of the aforementioned systems and methods, however, delivers a completely integrated user experience. In particular, visual representations of the various outputs are difficult to combine into a unified, easy to understand display. Thus, it is often left to the individual doctor or clinician to interpret multiple information streams at one time. However, data displayed on separate displays can become out of synch in a very short time, further complicating assimilation of information by the doctor or clinician.

BRIEF SUMMARY OF THE INVENTION

The present disclosure relates generally to medical systems configured to combine and synergize information in an expedient format for viewing on a display screen.

In one embodiment, a method for combining and synergizing data from different medical systems comprises obtaining from a first medical system an image disposed relative to a first coordinate system, obtaining from a second medical system supplemental data, synchronizing first and second clocks of the first and second medical systems, respectively, and displaying in synchronicity the supplemental data combined with the image.

In another embodiment, a system for combining and synergizing data from different medical systems comprises a computing device comprising a data input interface, a data output interface, processor resources, and memory resources. The memory resources store computer-readable instructions that, when executed by the processor resources, cause the processor resources to execute the following processes: obtain from a first medical system an image disposed in a first coordinate system through the data input interface; obtain from a second medical system supplemental data through the data input interface; synchronize first and second clocks of the first and second medical systems, respectively; and transmit to the data output interface data for displaying in synchronicity the supplemental data combined with the image.

In yet another embodiment, a method for synergizing data from different medical systems comprises obtaining location data from a first system, obtaining image data from a second system, co-registering coordinate systems from the first and second systems, synchronizing time domains from the first and second systems, displaying the location data in the image as a motion picture, and augmenting the motion picture with medical information from a third system.

In still another embodiment, a system for synergizing data from different medical systems comprises a first medical device configured to generate medical information correlated to a first time scale, and a medical positioning system comprising the following: a catheter configured to generate position data of a sensor relative to a magnetic coordinate system and a second time scale; circuitry configured to receive the position data, the medical information, and imaging data from an imager relative to an optical coordinate system and a third time scale, and further configured to synchronize the first, second, and third time scales; and a display unit configured to display real-time, time-synchronized imaging data, location data, and medical information.

DETAILED DESCRIPTION OF THE INVENTION

Figure 1:
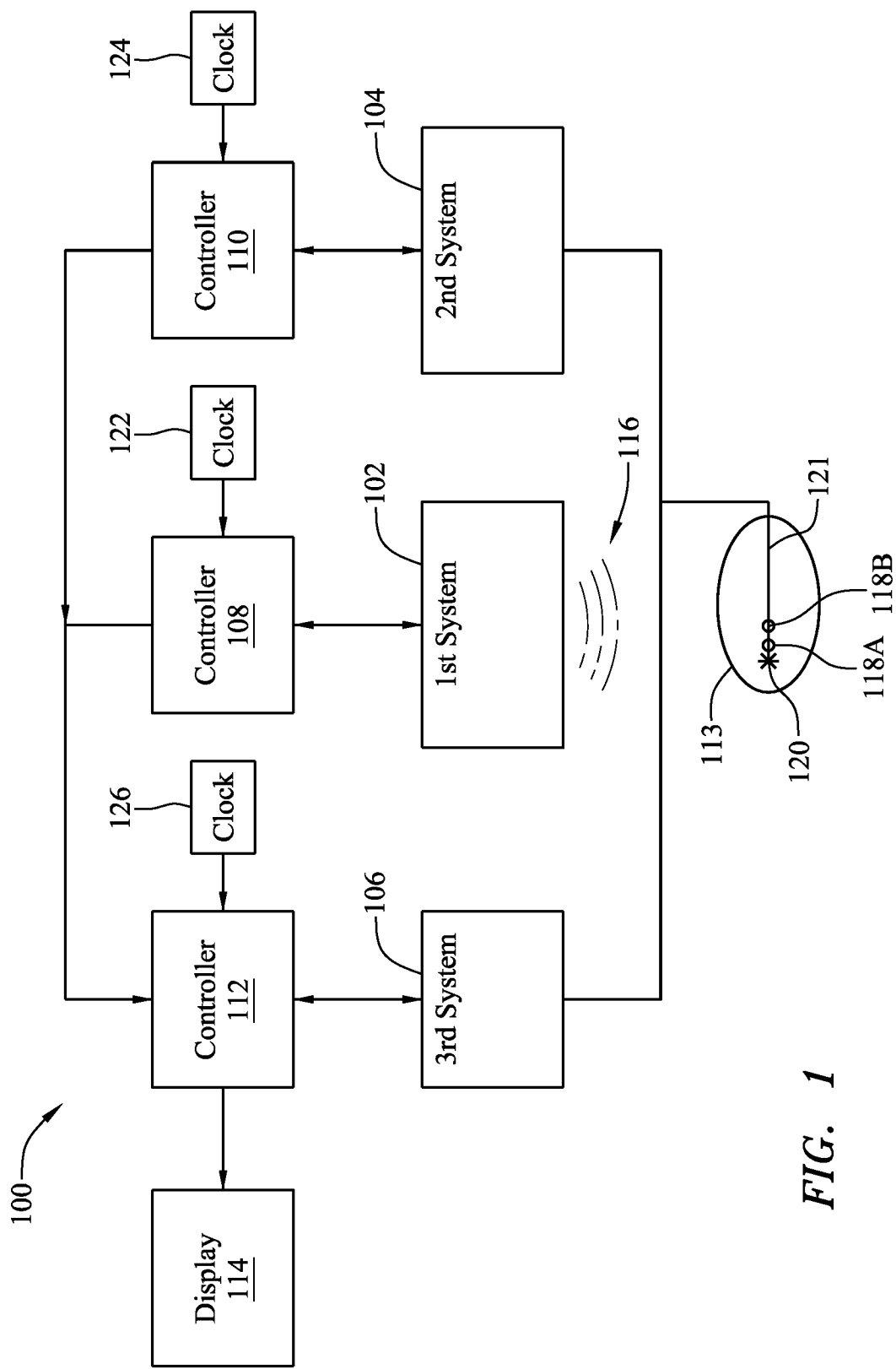
FIG. 1 is a schematic representation of a medical system configured to combine multiple independent data inputs into a synergized data output.

FIG. 1 is a schematic representation of medical system 100 configured to combine multiple independent data inputs into a synergized data output. Medical system 100 combines and synergizes data inputs from a plurality of sub-systems, including first system 102, second system 104 and third system 106. Sub-systems 102, 104, and 106 include controllers 108, 110, and 112, respectively. Data collected from each sub-system relative to patient 113 is presented at display 114 in an integrated, user-friendly format.

In the described embodiment, first system 102 comprises an imaging system, such as a fluoroscopic system that generates images using x-ray 116. In the described embodiment, second system 104 comprises a mapping and navigation system, such as an impedance-based system that generates data points using electrodes 118A and 118B. In the described embodiment, third system 106 comprises a mapping and navigation system, such as a magnetic-based system that generates data points using position sensor 120.

Electrodes 118A and 118B and position sensor 120 are shown mounted commonly on catheter 121. In other embodiments, electrodes 118A and 118B and position sensor 120 may be mounted on separate catheters.

In system 100, one or more of controllers 108-112 includes programming and instructions (e.g. computer readable instructions stored on a computer readable medium) for combining and synergizing data from systems 102-106, and presenting such data at display 114. For example, system 102 generates medical information relating to a two-dimensional image showing the expansion and contraction of heart wall tissue. For example, system 104 generates medical information relating to the location and movement of sensors relative to a heart wall represented as a three-dimensional model. For example, system 106 generates medical information relating to the location of a position sensor within three-dimensional space. Furthermore, controllers 108-112 include clocks 122-126, respectively, that generate timing information against which medical information from x-ray 116, electrodes 118A and 118B, and position sensor 120 is recorded, respectively. System 100 synchronizes the timing information so medical information from each medical system can be interpreted contemporaneously at display 114. Furthermore, system 100 integrates other aspects of data collected using x-ray 116, electrodes 118A and 118B, and position sensor 120, such as sampling rate, integration time, sensor accuracy, and the like. According to various aspects of the present disclosure, systems and methods for combining and synergizing medical information from different medical systems into a single display are described.

Figure 2:
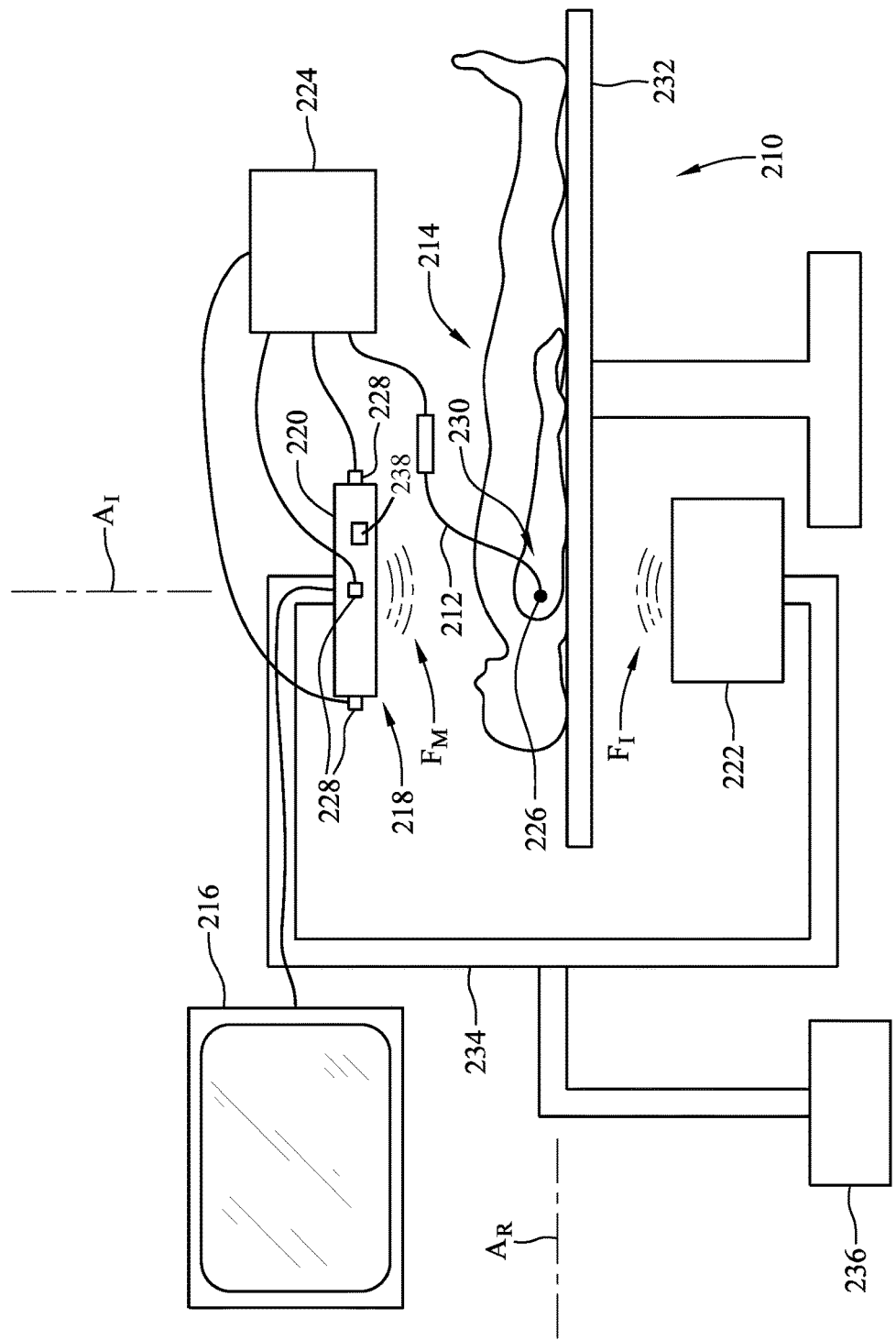
FIG. 2 is a schematic representation of a medical imaging system for generating and displaying the position of a sensor relative to an image on a display screen.
Figure 3:
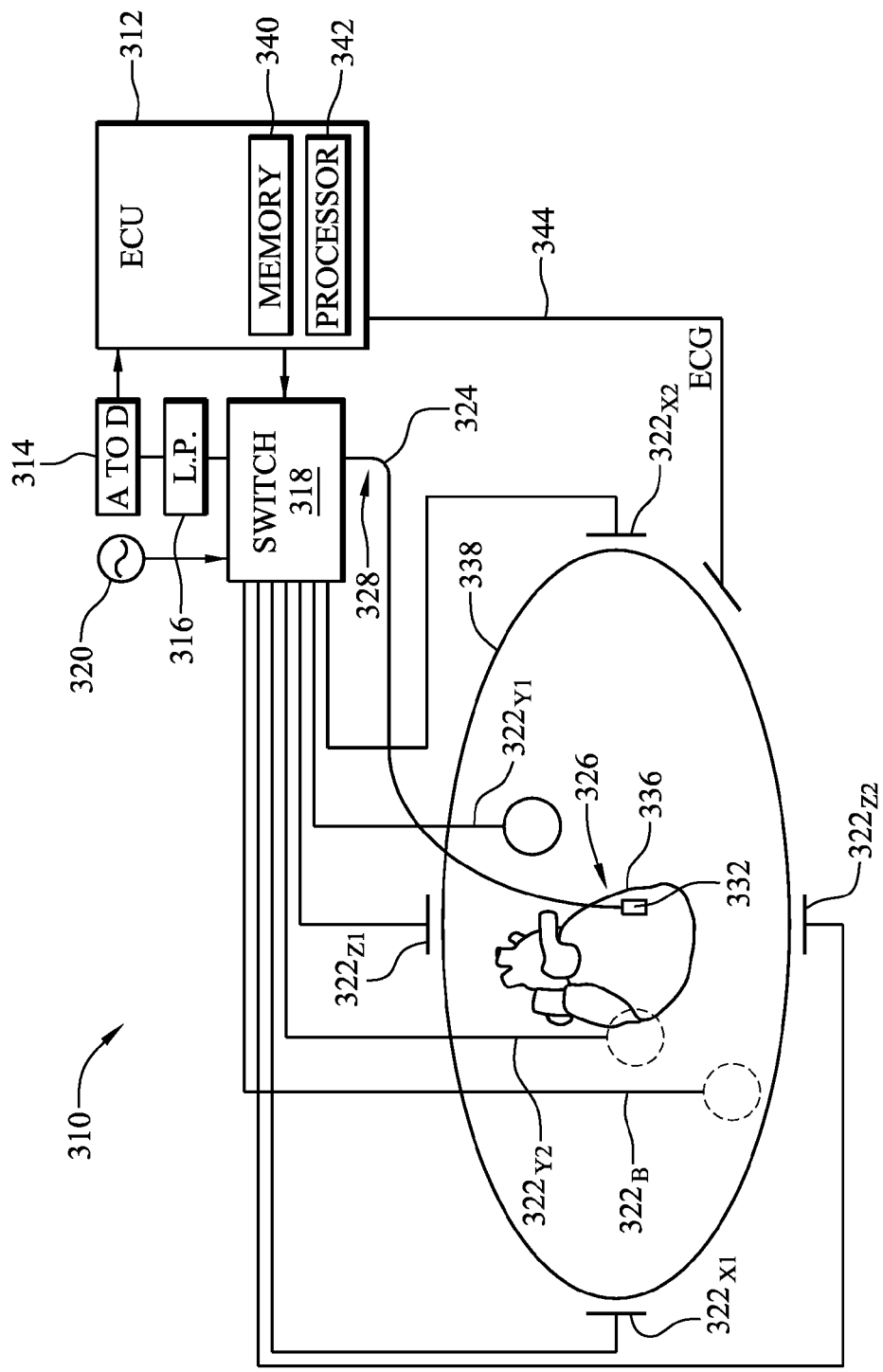
FIG. 3 is a schematic representation of a medical mapping and navigation system for generating and displaying the position of a sensor relative to a model on a display screen.
Figure 4A:
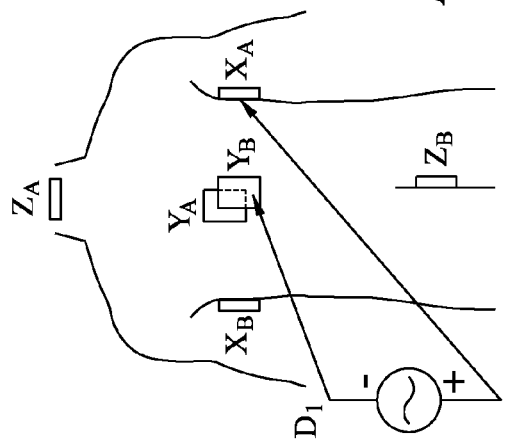
FIGS. 4A-4D are schematic representations of exemplary dipole pairs of driven body patch electrodes suitable for use with the medical mapping and navigation system of FIG. 3.
Figure 4B:
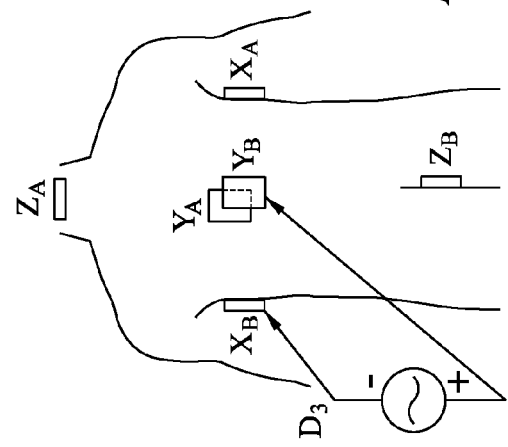
Figure 4C:
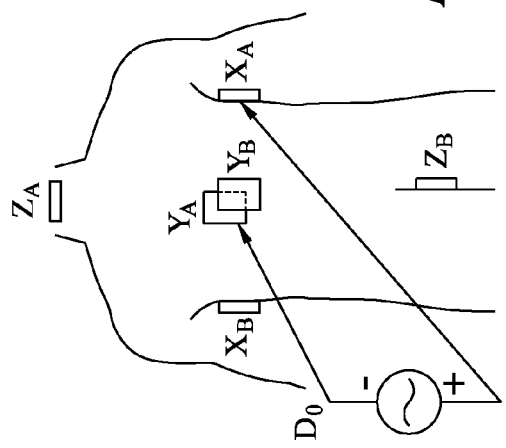
Figure 4D:
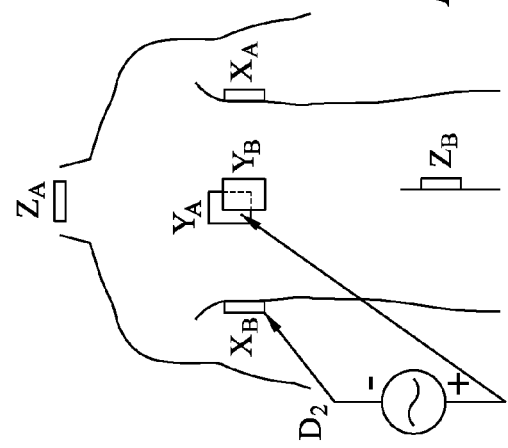
Figure 5:
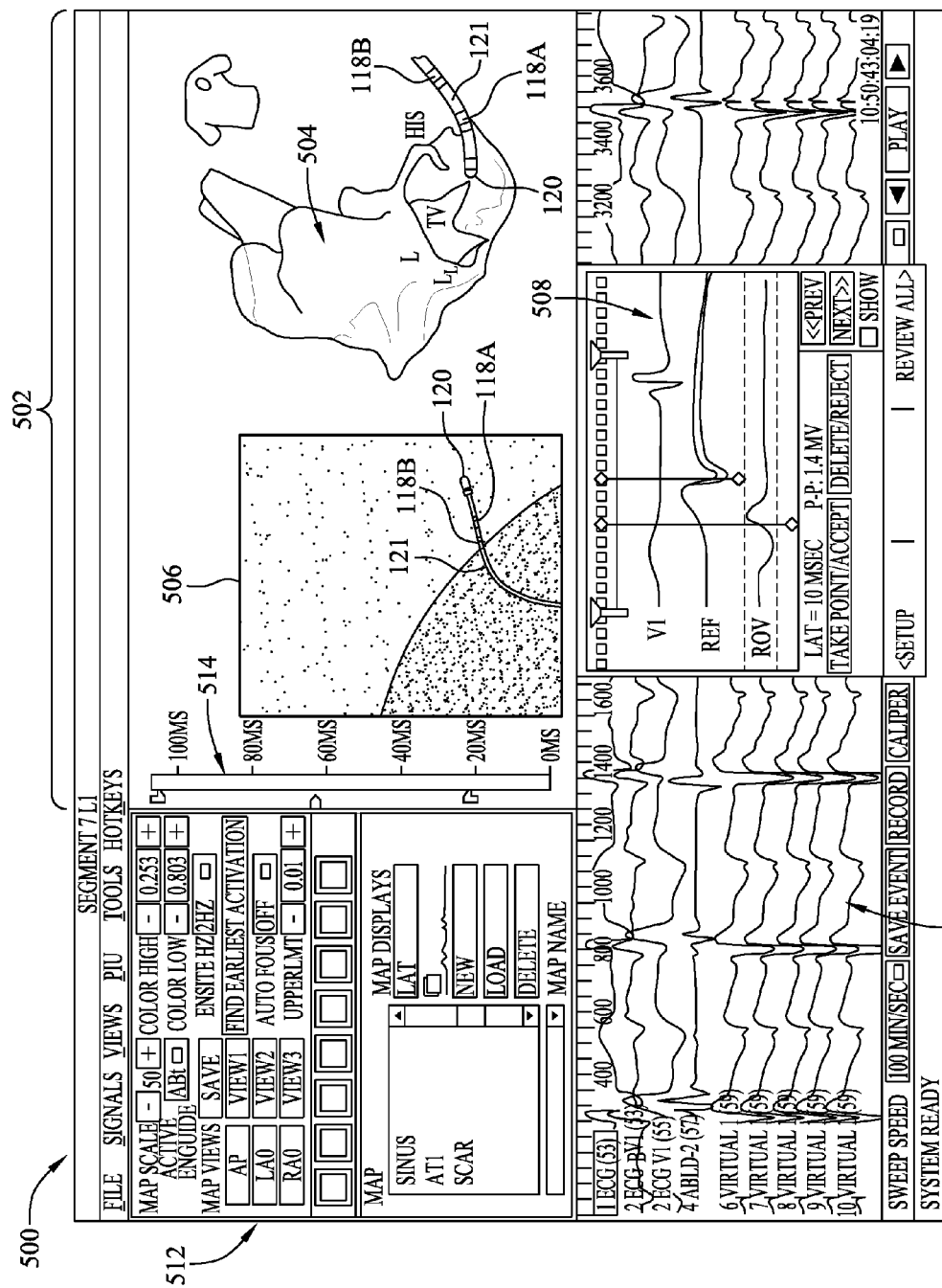
FIG. 5 is an exemplary display screen of the medical system of FIG. 1, showing data output from multiple independent medical systems synergized into a single view.
Figure 6:
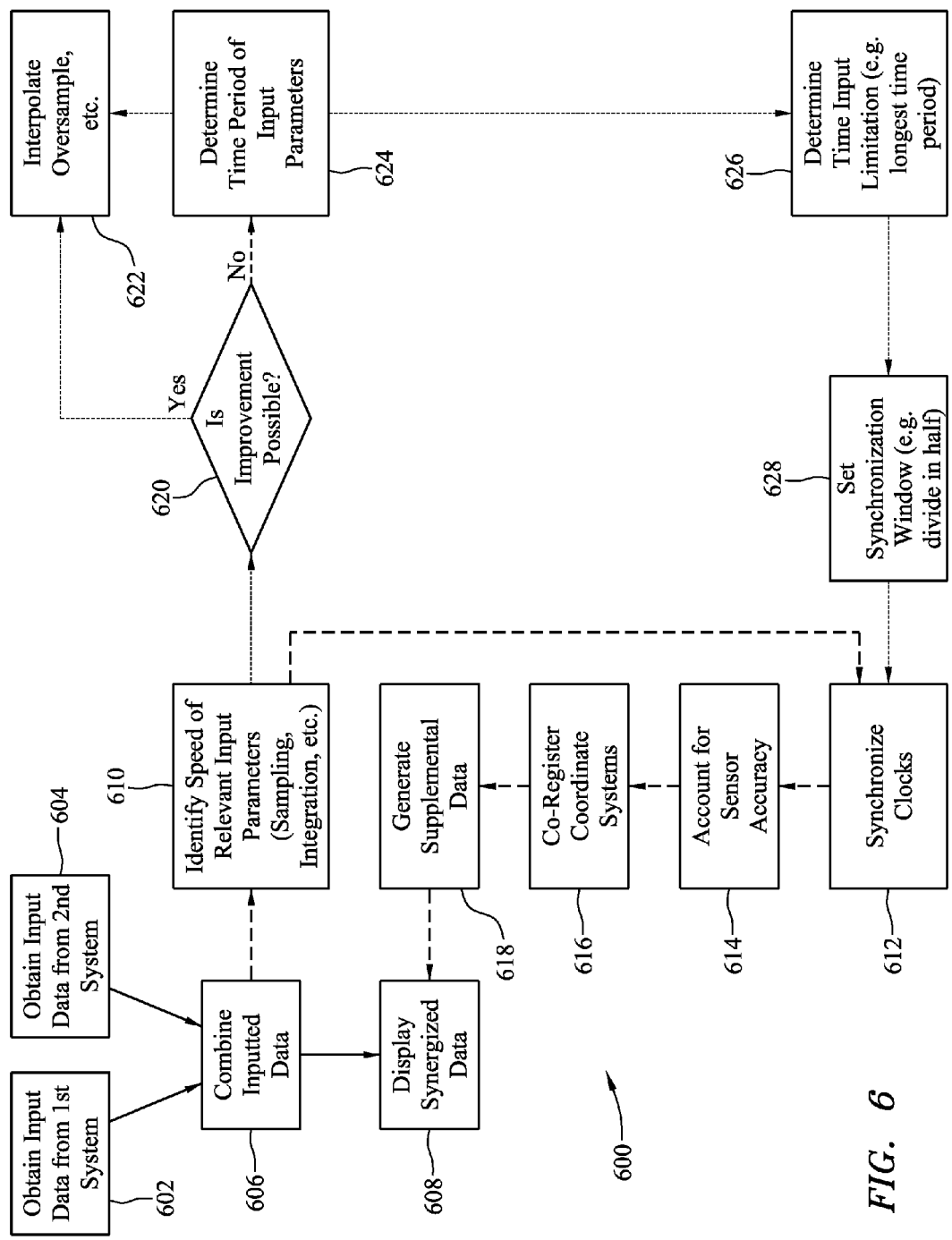
FIG. 6 is a flowchart diagramming one method of combining and synergizing data according to the present disclosure.
Figure 7:
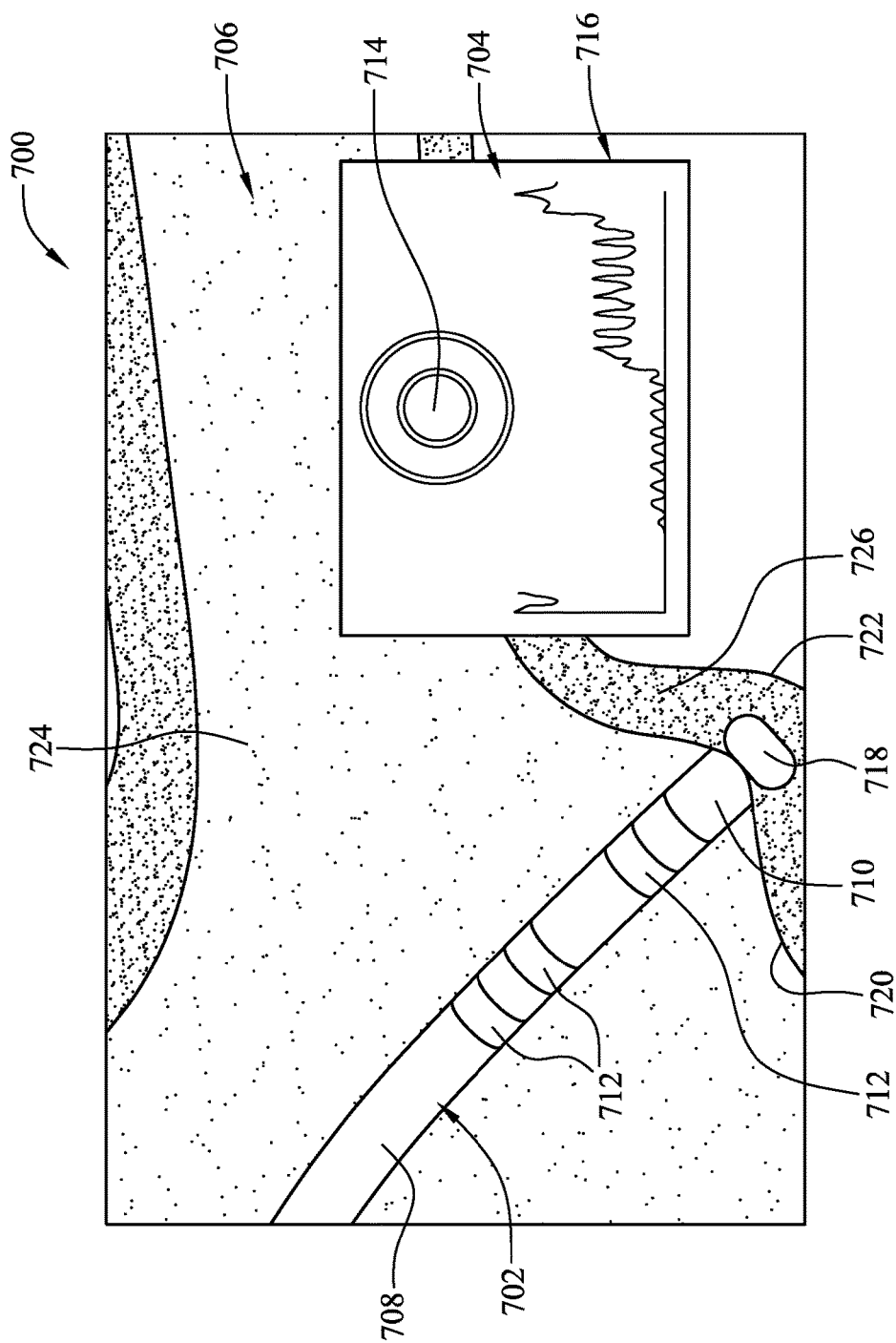
FIG. 7 is an exemplary display screen of data from a force-sensing ablation catheter being synergized into a fluoroscopic image.

FIG. 2 shows the structural integration of components of first system 102 and third system 106 from FIG. 1. FIGS. 3-4D show the components of second system 104, which can be structurally integrated into third system 106, such as is described in aforementioned U.S. Pub. No. 2012/0265054 A1 to Olson, which is hereby incorporated by reference in its entirety for all purposes. FIGS. 2-4D are described in order to provide an understanding of how each system generates data that is combined and synergized according to the present disclosure, such as described with reference to FIGS. 1 and 5-7. FIG. 5 is an exemplary display screen of the medical system of FIG. 1, showing data output from systems 102, 104, and 106 synergized into a single view. FIG. 6 is a flowchart diagramming one method of combining and synergizing data according to the present disclosure. FIG. 7 is an exemplary display screen showing another embodiment of combined and synergized information according to the systems and methods of the present disclosure.

FIG. 2 is a schematic representation of medical imaging system 210 for determining the position of catheter 212 relative to a model and an image of an organ of patient 214, as well as for generating and displaying supplemental medical information on display unit 216. System 210 includes moving imager 218, which includes intensifier 220 and emitter 222, and magnetic positioning system (MPS) 224, which includes position sensor 226 and field generators 228. Moving imager 218 generates an image of tissue from patient 214 on display unit 216, on which the location of position sensor 226 can be shown using MPS 224 to facilitate treatment and diagnosis of patient 214.

System 210 is configured to generate a two-dimensional fluoroscopic movie from moving imager 218 on which the location of position sensor 226 from MPS 224 can be shown. Moving imager 218 is representative of one embodiment of system 102 of FIG. 1. MPS 224 is representative of one embodiment of system 106 of FIG. 1. Specifically, in one embodiment, catheter 212 comprises catheter 121 of FIG. 1, and position sensor 226 comprises position sensor 120 of FIG. 1. Additional supplemental medical information can be shown on display unit 216 from a third medical system, such as system 104 of FIG. 1 or system 310 of FIG. 3.

Moving imager 218 is a device which acquires an image of region of interest 230 while patient 214 lies on operation table 232. Intensifier 220 and emitter 222 are mounted on C-arm 234, which is positioned using moving mechanism 236. In one embodiment, moving imager 218 comprises a fluoroscopic or X-ray type imaging system that generates a two-dimensional (2D) image of the heart of patient 214.

Magnetic positioning system (MPS) 224 includes a plurality of magnetic field generators 228 and catheter 212, to which position sensor 226 is mounted at a distal end. MPS 224 determines the position of the distal portion of catheter 212 in a magnetic coordinate system generated by field generators 228, according to output of position sensor 226. In one embodiment, MPS 224 comprises a MediGuide gMPS magnetic positioning system, as is commercially offered by St. Jude Medical, Inc., that simultaneously generates a three-dimensional (3D) model of the heart of patient 214. MPS 224 may include various input and output interfaces, non-volatile memory, and a processor configured to perform many of the functions and operations described herein.

C-arm 234 positions intensifier 220 above patient 214 and emitter 222 underneath operation table 232. Emitter 222 generates, and intensifier 220 receives, an imaging field $F_I$, e.g., a radiation field, that generates a 2D image of area of interest 230 on display unit 216. Intensifier 220 and emitter 222 of moving imager 218 are connected by C-arm 234 so as to be disposed at opposites sides of patient 214 along imaging axis $A_I$, which extends vertically with reference to FIG. 2 in the described embodiment. Moving mechanism 236 rotates C-arm 234 about rotation axis $A_R$, which extends horizontally with reference to FIG. 2 in the described embodiment. Moving mechanism 236 or an additional moving mechanism may be used to move C-arm 234 into other orientations. For example, C-arm 234 can be rotated about an axis (not shown) extending into the plane of FIG. 2 such that imaging axis $A_I$ is rotatable in the plane of FIG. 2. As such, moving imager 218 is associated with a 3D optical coordinate system having x-axis $X_I$, y-axis $Y_I$, and z-axis $Z_I$.

Magnetic positioning system (MPS) 224 is positioned to allow catheter 212 and field generators 228 to interact with system 210 through the use of appropriate wiring or wireless technology. Catheter 212 is inserted into the vasculature of patient 214 such that position sensor 226 is located at area of interest 230. Field generators 228 are mounted to intensifier 220 so as to be capable of generating magnetic field $F_M$ in area of interest 230 coextensive with imaging field $F_I$. MPS 224 is able to detect the presence of position sensor 226 within the magnetic field $F_M$. In one embodiment, position sensor 226 may include three mutually orthogonal coils, as described in U.S. Pat. No. 6,233,476 to Strommer et al., which is hereby incorporated by reference in its entirety for all purposes. As such, magnetic positioning system 224 is associated with a 3D magnetic coordinate system having x-axis $X_P$, y-axis $Y_P$, and z-axis $Z_P$.

The 3D optical coordinate system and the 3D magnetic coordinate system are independent of each other, that is they have different scales, origins and orientations, as well as different timing information. Movement of C-arm 234 via moving mechanism 236 allows imaging field $F_I$ and magnetic field $F_M$ to move relative to area of interest 230 within their respective coordinate system. However, field generators 228 are located on intensifier 220 so as to register the coordinate systems associated with moving imager 218 and MPS 224. Thus, images generated within each coordinate system can be merged into single image shown on display unit 216. Moving imager 218 and MPS 224 may function together as is described in U.S. Pub. No. 2008/0183071 A1 to Strommer et al., which is hereby incorporated by reference in its entirety for all purposes.

Display unit 216 is coupled with intensifier 220. Emitter 222 transmits radiation that passes through patient 214. The radiation is detected by intensifier 220 as a representation of the anatomy of area of interest 230. An image representing area of interest 230 is generated on display unit 216, including an image of catheter 212. C-arm 234 can be moved to obtain multiple 2D images of area of interest 230, each of which can be shown as a 2D image on display unit 216. The 2D images can be shown live to indicate real time movement of area of interest 230, such as the beating of a heart. Alternatively, a short loop of video (CINE) can be replayed over and over to simulate real time beating of the heart.

Display unit 216 is coupled to MPS 224. Field generators 228 transmit magnetic fields that are mutually orthogonal, corresponding to axes of the 3D magnetic coordinate system. Position sensor 226 detects the magnetic fields generated by field generators 228. The detected signals are related to the position and orientation of the distal end of catheter 212 by, for example, the Biot Savart law, known in the art. Thus, the precise position and location of the distal end of catheter 212 is obtained by MPS 224 and can be shown in conjunction with the 2D images of area of interest 230 at display unit 216. Furthermore, data from position sensor 226 can be used to generate a 3D model of area of interest 230, as is described in U.S. Pat. No. 7,386,339 to Strommer et al., which is hereby incorporated by reference in its entirety for all purposes.

In accordance with yet another embodiment of the present teachings, information regarding the position of medical imaging system 210 and/or other information associated imaging system 210 may be obtained by sensing the activation of imaging system 210 and, in particular, the existence of radiation from emitter 222. Radiation emissions may be detected using radiation detection sensor 238, such as the XB8816 Series sensor offered for sale by X-Scan Imaging Corporation. MPS 224 or controller 108 may be configured to determine a time associated with the radiation emission responsive to a signal generated by radiation detector sensor 238 and thereby synchronize signals generated by other sensors such as position sensor 226, position sensors 120 and electrodes 118A and 118B. For example, X-rays may be generated up to sixty times per second, so it is important to know exactly when each X-ray frame was taken in order to accurately match the location of other sensors in the frame. Otherwise, if the time at which emitter 222 is on is unknown, or not precisely known, the location of position sensor 226, for example, can lag its real-time location in display unit 216. Thus, for example, a quarter second error in knowing when emitter 222 is active may produce a large error in position. In synchronizing time data generated by radiation detection sensor 238 and position sensor 226, imaging system 210 can accurately plot the location of sensor 226 in the X-ray frame. Additionally, radiation detection sensor 238 may be used so that imaging system 210 can determine when emitter 222 is inactive in order to facilitate more accurate collection of data, such as from position sensor 226. For example, magnetic field generators 28 can be activated when emitter 222 is off in order to reduce interference in magnetic field FM by the X-rays. Additional description of such features are described in Int. Pub. No. WO/2014/141113 A2 to Eichler et al. and U.S. Pub. No. 2008/0319312 A1 to Eichler et al., both of which are hereby incorporated by reference in their entireties for all purposes.

Images and data generated by system 210 can be used to facilitate various medical procedures. For example, catheters enabled with positioning sensors are effective in performing ablation procedures with the aid of fluoroscopy. However, not all data relevant to performing an ablation procedure is visible from data and images generated by moving imager 218 and magnetic positioning system 224. For example, certain physiological data, such as electrograms from an impedance enabled system or an EP recording system may be useful in providing feedback about the patient undergoing the procedure. Additionally, lesion assessment information from a force sensing catheter may be useful in providing real-time assessment of the ablation process, as is described in U.S. Pat. No. 8,641,705 to Leo et al., which is hereby incorporated by reference in its entirety for all purposes. Force sensing catheters are commercially available from St. Jude Medical, Inc. under the name TactiCath™ Quartz which may be used in connection with the TactiSys™ Quartz system. Thus, diagnosis and treatment of patient 214 can be encumbered by the doctor or clinician having to mentally synergize information on different displays from different medical systems.

The present disclosure provides systems and methods for combining medical data generated by moving imager 218 and MPS 224 of system 210 with other supplemental medical data obtained from a third medical system. The combined medical data increases the usefulness of information generated by the aggregate system, such as system 100 of FIG. 1, and improves the effectiveness of the medical diagnoses and procedures performed with the aggregate system.

FIG. 3 is a schematic representation of an embodiment of exemplary mapping and navigation system 310 that generates medical information that can be combined and synergized with supplemental medical information from another system. System 310 may include various visualization, mapping and navigation components as known in the art, including, for example, an EnSite™ Velocity™ system utilizing EnSite™ NavX™ technology commercially available from St. Jude Medical, Inc., or as seen generally, for example, by reference to U.S. Pat. No. 7,263,397, or U.S. Pub. No. 2007/0060833, both of which are hereby incorporated by reference in their entireties for all purposes.

System 310 may include an electronic control unit (ECU) 312, analog-to-digital converter (A-to-D) 314, low-pass filter (L.P.) 316, switch 318, signal generator 320, and a plurality of body surface patch electrodes 322. System 310 may be electronically and/or mechanically coupled with an elongate medical device, such as, in one embodiment, a contact or non-contact mapping catheter (e.g., cardiac mapping catheter 324). Catheter 324 includes distal end portion 326 and proximal end portion 328. Distal end portion 326 includes electrode 332 and extends into heart 336 of patient 338. Proximal end portion 328 connects catheter 324 to switch 318.

With reference to the present disclosure, system 310 is configured to, among other things, collect cardiologic data and location data, particularly electrocardiogram information relative to a three-dimensional (3D) model of a heart, and to combine and synergize such data with information from system 210 of FIG. 2. For example, electrode 332 from catheter 324 of system 310 can be incorporated into a rendering of a shaft including position sensor 226, which are then overlaid onto an image from moving imager 218. In one embodiment, catheter 324 comprises catheter 212 of FIG. 2 with the addition of electrode 332. In another embodiment, catheter 324 comprises catheter 121 (along with position sensor 120) of FIG. 1 and electrode 332 represents electrodes 118A and 118B.

System 310 may be configured to provide, among other things, mapping of patient tissue, such as one or more chambers of heart 336 of patient 338, and a 3D model bearing the surface geometry of the mapped tissue. Accordingly, ECU 312 may be configured to receive electrical measurements from one or more electrodes (diagrammatically shown as a single electrode 332 in FIG. 1) on mapping catheter 324 and, based on those measurements, to assess one or more electrical characteristics of tissue surrounding the distal end of mapping catheter 324. In an embodiment, ECU 12 may be configured to determine a voltage distribution of an endocardial surface according to electrical measurements from mapping catheter electrode 332. ECU 312 may be further configured to determine that voltage distribution with respect to an anatomical model, such as a model of one or more chambers, features, and/or surfaces of heart 336.

ECU 312 may include various input and output interfaces, non-volatile memory 340, and processor 342 configured to perform many of the functions and operations described herein—i.e., memory 340 may store instructions for performing portions of one or more methods or processes described herein, and processor 342 may be configured to execute those instructions to perform the methods or processes. Memory 340 may also be configured to store an anatomical model, such as a cardiac chamber model, a plurality of measurements from mapping catheter 324, a plurality of terms and values for the methods described below, and other data and information. In an embodiment, ECU 312 may additionally or alternatively comprise a field-programmable gate array (FPGA) and/or other known computing device.

In addition to (and as a part of) electrophysiology mapping, system 10 may be configured to determine the position and orientation (P&O) of mapping catheter 324 (e.g., of distal end portion 326) within patient 338. Accordingly, ECU 312 may be configured to control generation of one or more electrical fields and determine the position of one or more electrodes (e.g., electrode 332) within those fields. ECU 312 may thus be configured to control signal generator 20 in accordance with predetermined strategies to selectively energize various pairs (dipoles) of body surface patch electrodes 322, as described in greater detail below. In operation, ECU 312 may (1) obtain raw patch data (i.e., voltage readings) via filter 316 and A-to-D converter 314 and (2) use the raw patch data (in conjunction with electrode measurements) to determine the raw, uncompensated, electrode location coordinates of electrode 332 positioned inside heart 336 or a chamber thereof in three-dimensional space. ECU 312 may be further configured to perform one or more compensation and adjustment functions, and to output a location of electrode 332. Motion compensation may include, for example, compensation for respiration-induced patient body movement, as described in U.S. Pub. No. 2012/0172702 A1 to Koyrakh et al., which is hereby incorporated by reference in its entirety for all purposes.

Body surface patch electrodes 322 may be used to generate axes-specific electric fields within patient 338, and more specifically within heart 336. Three sets of patch electrodes may be provided: (1) electrodes 322X1, 322X2, (X-axis); (2) electrodes 322Y1, 322Y2, (Y-axis); and (3) electrodes 322Z1, 322Z2, (Z-axis). Additionally, a body surface electrode ("belly patch") 322B, may be provided as an electrical reference. Other surface electrode configurations and combinations are suitable for use with the present disclosure, including fewer electrodes 322, more electrodes 322, or different physical arrangements, e.g. a linear arrangement instead of an orthogonal arrangement.

Each patch electrode 322 may be independently coupled to switch 318, and pairs of patch electrodes 322 may be selected by software running on ECU 312 to couple patch electrodes 322 to signal generator 320. A pair of electrodes, for example the Z-axis electrodes 322Z1, 322Z2, may be excited by signal generator 320 to generate an electrical field in patient 338 of the patient and, more particularly, within heart 336. In one embodiment, this electrode excitation process occurs rapidly and sequentially as different sets of patch electrodes 322 are selected and one or more of the unexcited surface electrodes 322 are used to measure voltages. During the delivery of the excitation signal (e.g., current pulse), the remaining (unexcited) patch electrodes 322 may be referenced to belly patch 322B and the voltages impressed on these remaining electrodes 322 may be measured. In this fashion, patch electrodes 322 may be divided into driven and non-driven electrode sets. Low pass filter 316 may process the voltage measurements. The filtered voltage measurements may be transformed to digital data by analog to digital converter 314 and transmitted to ECU 312 for storage (e.g. in memory 340) under the direction of software. This collection of voltage measurements may be referred to herein as the "patch data." The software may have access to each individual voltage measurement made at each surface electrode 322 during each excitation of each pair of surface electrodes 322.

The patch data may be used, along with measurements made at electrode 332, to determine a relative location of electrode 332. The patch data may also be used along with measurements made at electrode 332 and/or other electrodes on catheter 324, such as a tip electrode, or on another device to determine a relative location of electrode 332 and/or the other electrodes. The discussion above and below describes determining the location of electrode 332, but it should be understood to apply to a tip electrode and other electrodes, as well. In some embodiments, potentials across each of the six orthogonal patch electrodes 322 may be acquired for all samples except when a particular surface electrode pair is driven. In embodiments, sampling a voltage with a particular patch electrode 322 while a surface electrode 322 acts as a source or sink in a driven pair may be avoided, as the potential measured at a driven electrode during this time may be skewed by the electrode impedance and the effects of high local current density. In an alternate embodiment, however, sampling may occur at all patch electrodes 322, even those being driven.

Generally, in an embodiment, three nominally orthogonal electric fields may be generated by a series of driven and sensed electric dipoles in order to determine the location of catheter 324 (i.e., of electrode 332). Alternately, these orthogonal fields can be decomposed and any pair of surface electrodes (e.g., non-orthogonal) may be driven as dipoles to provide effective electrode triangulation.

FIGS. 4A-4D show a plurality of exemplary non-orthogonal dipoles, designated D0, D1, D2 and D3. In FIGS. 4A-4D, the X-axis surface electrodes are designated XA and XB, the Y-axis surface electrodes are designated YA and YB, and the Z-axis electrodes are designated ZA and ZB. For any desired axis, the potentials measured across an intra-cardiac electrode 332 resulting from a predetermined set of drive (source-sink) configurations may be combined algebraically to yield the same effective potential as would be obtained by simply driving a uniform current along the orthogonal axes. Any two of patch electrodes 322 may be selected as a dipole source and drain, as noted above, with respect to a ground reference, e.g., belly patch 322B, while the unexcited body patch electrodes 322 measure voltage with respect to the ground reference. Electrode 332 placed in heart 336 is also exposed to the field from a current pulse, and voltages on electrode 332 are individually and separately measured with respect to ground, e.g., belly patch 322B.

Referring again to FIG. 3, data sets from each of patch electrodes 322 and electrode 332 are all used to determine the location of electrode 332 within heart 336. After the voltage measurements are made for a particular set of driven patch electrodes 322, a different pair of patch electrodes 322 may be excited by signal generator 320 and the voltage measurement process of the remaining patch electrodes 322 and electrode 332 takes place. The sequence may occur rapidly, e.g., on the order of one hundred times per second in an embodiment. To a first approximation the voltage on electrode 332 within heart 336 bears a linear relationship with position between patch electrodes 322 that establish the field within heart 336, as more fully described in U.S. Pat. No. 7,263,397 referred to above.

Some or all of the conventional twelve (12) ECG leads, coupled to additional body patches and designated collectively by reference numeral 344, may be provided to support the acquisition of an electrocardiogram (ECG) of the patient. As shown, ECG leads 344 may be coupled directly to the ECU 312 for acquisition and subsequent processing to obtain the phase of the heart in the cardiac cycle. Cardiac phase information may be used, in an embodiment, in mapping of electrical activity of heart 336, as described below.

In summary, FIG. 3 shows an exemplary system 310 that employs seven body patch electrodes 322, which may be used for injecting current and sensing resultant voltages. Current may be driven between two patches 322 at any time. Measurements may be performed between non-driven patch 322 and, for example, belly patch 322B as a ground reference. A patch bio-impedance, also referred to as a "patch impedance", may be computed according to the following equation:

$$BioZ[n \to m][k] = \frac{V_k}{I_{n \to m}}$$

where $V_k$ is the voltage measured on patch k and $I_{n \to m}$ is a known constant current driven between patches n and m. The position of electrode 332 may be determined by driving current between different sets of patches and measuring one or more patch impedances. In one embodiment, time division multiplexing may be used to drive and measure all quantities of interest. Position determining procedures are described in more detail in, for example, U.S. Pat. No. 7,263,397 and U.S. Pub. No. 2007/0060833 A1 referred to above. To perform an electrophysiology (e.g., mapping) procedure, distal end portion 326 of catheter 324 or multiple such catheters 324 may be manually guided to a desired location by a user such as a physician. In addition to determining the positions of electrode 332, system 310 may also be configured to assess the electrical activity of the heart. Accordingly, ECU 312 may be further configured to perform one or more steps in one or more methods of determining a voltage distribution on a cardiac surface.

As briefly mentioned above, ECU 312 is configured to generate a three-dimensional (3D) surface geometry or 3D model of heart 336. ECU 312 also shows the location of electrode 332 relative to the 3D model of heart 336. ECU 312 additionally may output data relating to electrode 332 and the 3D model of heart 336 to MPS 224 (FIG. 2) so that, for example, the locations of electrode 332 and position sensor 226 can be shown relative to the image of moving imager 218, as shown in FIG. 5.

FIG. 5 shows an exemplary computer display 500 that can be connected to ECU 312 of FIG. 3, MPS 224 of FIG. 2, and moving imager 218 of FIG. 2. Thus, display 500 may comprise display 114 of FIG. 1 or display unit 216 of FIG. 2. Display 500 is used to show data to a user of system 100, and to present certain options that allow the user to tailor system configuration for a particular use. It should be noted that the contents on the display can be easily modified and the specific data presented is illustrative and not limiting of the invention. Image panel 502 shows 3D model 504 of a heart chamber generated by, for example, ECU 312. Image panel 502 additionally shows image 506 of the heart chamber generated by, for example, moving imager 218.

Catheter 121, position sensor 120 and electrodes 118A and 118B are shown on 3D model 504 and image 506. With respect to model 504 generated by system 104, data relative to position sensor 120 generated by system 106 is synergized with data relative to electrodes 118A and 118B generated by system 104, for example. Likewise, with respect to image 506 generated by system 102, data relative to electrodes 118A and 118B generated by system 104 is synergized with data relative to position sensor 120 generated by system 106, for example.

3D model 504 and image 506 are simultaneously displayed in image panel 502. However, either of 3D model 504 or image 506 may be displayed individually. In FIG. 5, 3D model 504 is shown as a left atrium, but may comprise any heart chamber such as a ventricle. Additionally, system 100 may be used to map other chambers or hulls of patient 113 (FIG. 1) that can be displayed on image panel 502 as a 3D model.

Display 500 also shows electrical activity of a heart of patient 113 (FIG. 1), such as the voltages associated with wave fronts 508. The electrical activity can also be shown as ECG information 510. The particulars of 3D model 504 (e.g. rotation, size, etc.), image 506 (e.g. loop, resolution, orientation, etc.) and ECG information 510 (electrograms, QRS, etc.) can be specified and/or changed at user panel 512.

3D model 504 comprises a collection of data points gathered by electrodes 118A and 118B within patient 113, and interpolated by controller 110. 3D model 504 includes "isochrones" in false color (not shown) with guide bar 514, which may also be represented as wave fronts (not shown) on 3D model 504 in the same false color indicated by guide bar 514. In the embodiment of FIG. 5, 3D model 504 and the location of electrodes 118A and 118B may be generated using catheter 121 in a similar fashion as was described with reference to catheter 324 of FIG. 3.

Image 506 comprises an X-ray image of tissue of patient 113. In one embodiment, image 506 may comprise a live fluoroscopic moving image. In another embodiment, image 506 may comprise a CINE, which is a recorded loop of a short duration of live fluoroscopy encompassing, for example, at least one cycle of a heartbeat. In one embodiment, image 506 may include supplemental medical data, such as shading corresponding to guide bar 514 to show wave fronts. In the embodiment of FIG. 5, image 506 may be generated in a similar fashion as was described with reference to moving imager 218 of FIG. 2. In the embodiment of FIG. 5, the location of position sensor 120 may be generated using catheter 121 in a similar fashion as was described with reference to catheter 212 of FIG. 2.

System 100 is able to combine and synergize the output of systems 102, 104, and 106 to obtain and display information in a way that is not possible by the use of such systems separately. Thus, not only can information from one system by imported into a display of another system, the combined information can be augmented with new information only possible when the combined information is synergized. For example, the location of position sensor 120 on model 504 is combined with the locations of electrodes 118A and 118B. Similarly, the locations of electrodes 118A and 118B on image 506 are combined with the location of position sensor 120. Furthermore, the presence of catheter 121 in model 504 is synergized, as an artifact, with electrodes 118A and 118B and position sensor 120. Artifacts and other supplemental medical information, such as physiological information, force information, pressure information and the like, may be combined and synergized into data shown on display 500 using the systems and methods described herein.

The systems and methods of the present disclosure combine and synergize information by, for example, improving sampling rates, synchronizing processor clocks, resolving sensor image outputs, and the like, as is discussed with reference to FIG. 6. Combining and synergizing of information pursuant to the present disclosure generates a display that facilitates treatment and diagnosis of patient 113. For example, the timing of information generated by systems 102, 104, and 106 is displayed contemporaneously so that activity relating to position sensor 120 and electrodes 118A and 118B can be observed simultaneously with ECG information 510 and wave fronts 508. Additionally, the three dimensional accuracy of model 504 can be resolved with the two-dimensional image accuracy of image 506 to yield, for example, better soft tissue definition in model 504. One way of resolving the images is by projecting model 504 onto image 506, fixing the projection boundaries according to the resolution of image 506, and then imposing those fixes back onto model 504. In another embodiment, several of images 506 taken at different orientations can be projected onto model 504 in commensurate orientations. It is also possible to perform clustering or segmentation algorithms on image 506 and on model 504, and then matching the projected segments of image 506 to the segments in model 504. Another way to improve model 504 is by projecting image 506 onto it. This enables a doctor or clinician to more accurately evaluate information without having to guess or mentally combine information.

In an embodiment, one or more of the steps of the methods described below (e.g. with reference to FIG. 6) may be performed by controller 108, controller 110, controller 112, MPS 224 or ECU 312 (e.g., embodied in computer readable instructions stored in memory 40 and executed by processor 42) to generate 3D model 504, image 506 and the locations of electrodes 118A and 118B, and position sensor 120.

FIG. 6 is a flowchart diagramming one method of combining and synergizing data according to the present disclosure. As indicated by solid arrows, method 600 of the present disclosure nominally relates to obtaining two inputs 602 and 604 from different medical systems, combining the inputs at step 606, and outputting synergized data on a display at step 608. Although described with respect to two inputs, the method of the present disclosure contemplates synergizing three or more inputs.

As indicated by dashed arrows in FIG. 6, combining the data at step 606 nominally comprises identifying speed of the relevant parameters of the inputs at step 610, synchronizing clocks of the input medical systems at step 612, accounting for sensor spatial accuracy at step 614, co-registering coordinate systems of the input medical systems at step 616, and generating supplemental data at step 618. Displaying synergized data at step 608 involves outputting the combined information in a unified display, as well as showing other information not available from any single system alone.

As indicated by dotted arrows in FIG. 6, in one embodiment, synchronizing the clocks of the input medical systems at step 612 comprises the steps of:

a) Determining if improvement of input parameters is possible at step 620;
b) Interpolating or oversampling if possible at step 622;
c) Determining the time periods of the input parameters at step 624;
d) Determining a Time Input Limitation at step 626; and
e) Determining a Synchronization Window at step 628.

By way of a primary example, medical system inputs 602 and 604 may comprise image data from imaging system 102 (FIG. 1), such as a fluoroscopic x-ray image, and location data from mapping system 104 (FIG. 1), such as the location of an impedance-based position sensor, respectively. Relevant input parameters of step 610 comprise sampling rate, sensor integration times, and other parameters dependent on the time it takes to perform a function, e.g. process light for an image input, process impedance data for a location input, etc. In the primary example, imaging system 102 of FIG. 1 may have a sampling rate of approximately 30 Hz (cycles per second), which translates to a sampling time of about 33 milliseconds, and may have a sensor integration time of approximately 4 milliseconds. Also in the primary example, mapping system 104 of FIG. 1 may have a sampling rate of approximately 100 Hz, which translates to a sampling time of about 10 milliseconds, and may have a sensor integration time of approximately 4 milliseconds.

Table 1 provides a non-exhaustive, exemplary list of medical systems that can be combined and synergized according to the present disclosure. The approximate sampling rate and sampling time (period) for various medical systems are summarized in Table 1. Values listed in Table 1 are provided as examples for the sake of instruction and actual values may be different. Sampling rates and various other time-related parameters for the medical systems can be stored in memory within, for example, ECU 312, Controller 112, or the like.

At step 620, the input parameters are evaluated to determine if improvements to the various rates can be made. In the primary example, if imaging system 102 comprises an x-ray generated image, it is not possible to interpolate between images, but, the location of electrodes 118A and 118B in system 104 can be interpolated between raw data points from the electrodes. However, since the sampling time of imaging system 102 is already the slowest system, improving the sampling time (decreasing the time between samples) of mapping system 104 is not beneficial.

As another example, if data from a MediGuide system and an EnSite system were to be synergized, it would be possible to improve the data. When used together, a MediGuide system has a slower period as compared to an EnSite system. Thus, we could artificially increase the sampling rate of a MediGuide system by, for example, interpolating the raw data generated by the system. In one embodiment, a linear interpolation technique is used to average two magnetic position data points $x_1$ and $x_2$ at adjacent times $t_1$ and $t_2$ to obtain an estimated magnetic position data point $x(t-x_1)/(x_2-x_1)$ at time t, where $t_1<t<t_2$. By interpolating data for the MediGuide system, the sampling rate would increase and, moreover, it could be matched to the EnSite system timing. Thus, the sampling time for each of the systems could be matched so that data is displayed together. For example, a graph of sampled values could be displayed on a common time axis, wherein the time axis will have a uniform spacing according to the period of the EnSite system. Also, with identical sample rates, the MediGuide system data and the EnSite system data can be filtered in an identical manner.

Standard interpolation techniques may be used, such as piecewise constant interpolation, linear interpolation, polynomial interpolation and spline interpolation, at step 622. Alternatively to interpolation, other methods may be used to artificially increase the sampling rate of a system. For example, oversampling or extrapolation methods could be used. Suitable interpolation, oversampling and extrapolation methods are known in the art.

Alternatively to improving data from the slowest system, data from faster systems can be brought down to the lowest common denominator by, for example, filtering the faster systems to bring all data to the longer time.

After any data improvement techniques are performed, the sampling time (period) for each input parameter is determined for each system at step 624. This may simply involve converting sampling rates to sampling times, as is shown in Table 1. Next, the Time Input Limitation is determined at step 626. The Time Input Limitation is simply the slowest input parameter of the combined systems, e.g. the input parameter that other systems would need to wait on in order to provide simultaneous, real-time data. In the described embodiment, the slowest system parameter (i.e. longest period) is selected at step 626 to be the Time Input

TABLE 1

Sampling Speeds of Various Medical Systems

| System | MediGuide | X-Ray | EnSite | TactiSys Quartz | WorkMate Claris | Ultrasound |
|---|---|---|---|---|---|---|
| Sampling Rate (Hz) | 100 (nominal) 30 (with EnSite) 15 (with X-ray) | 30 (nominal) 60 (with CINE) | 100 | 50 | 200 | 42 |
| Period (milliseconds) | 10 (nominal) 33 (with Ensite) 67 (with X-ray) | 33 (nominal) 17 (with CINE) | 10 | 20 | 5 | 23 |

Limitation. Continuing with the primary example, if imaging system 102 has a sampling time of 33 milliseconds, and mapping system 104 has a sampling time of 10 milliseconds, 33 milliseconds is the Time Input Limitation of integrated system 100 (given integration times of 4 milliseconds for both systems). In other examples, the integration time of a sensor may be slower than the sampling rate and thus comprise the Time Input Limitation.

By way of another example, three systems can be analyzed by adding a MediGuide system to the primary example. In such a scenario, the MediGuide system sampling rate would be 15 Hz, the X-Ray sampling rate would be 60 Hz, and the EnSite system sampling rate would be 100 Hz. The associated sampling times would be 67 milliseconds, 17 milliseconds, and 10 milliseconds, respectively. The MediGuide system takes the longest period of time to obtain one data point or set of data points—it has the slowest sampling rate. Thus, the Time Input Limitation would be 67 milliseconds from the MediGuide system.

The approximate Time Input Limitations for various medical system pairings (i.e. two systems of Table 1) are summarized in Table 2. Values listed in Table 2 are provided as examples for the sake of instruction and actual values may be different.

TABLE 2

| | Time Input Limitations (milliseconds) | | | | | |
|---|---|---|---|---|---|---|
| System | MediGuide 10 33 (Ensite) 67 (X-ray) | X-Ray 17 (CINE) | EnSite 10 | TactiSys Quartz 20 | WorkMate Claris 5 | Ultrasound 23 |
| MediGuide 10 33 (Ensite) 67 (X-ray) | - | 33.5 | 17 | 10 | 5 | 12.5 |
| X-Ray 17 (CINE) | 33.5 | - | 8.5 | 10 | 8.5 | 12.5 |
| EnSite 10 | 17 | 8.5 | - | 10 | 5 | 12.5 |
| TactiSys Quartz 20 | 10 | 10 | 10 | - | 10 | 12.5 |
| WorkMate Claris 5 | 5 | 8.5 | 5 | 10 | - | 12.5 |
| Ultrasound 23 | 12.5 | 12.5 | 12.5 | 12.5 | 12.5 | - |

Generally, it is desirable that system 100 stay synchronized within one period of the Time Input Limitation. In one embodiment, the period of the Time Input Limitation is cut to a common devisor, such as one-half, one-quarter, one-tenth, etc., to determine the Synchronization Window at step 628 for any two paired systems. Thus, for the primary example, in order to ensure that each system stays synchronized for an acceptable amount of time, the Synchronization Window for the Time Input Limitation is set to approximately 17 milliseconds (~33 milliseconds÷2).

At step 612, clocks 122, 124, and 126 (FIG. 1) are synchronized based on the Time Input Limitation and Synchronization Window so that a common global time is obtained. Common time synchronization methods can be used, such as Cristian's algorithm, Network Time Protocol (NTP) methods, and Precision Time Protocol (PTP) methods. Such methods are employed to begin the data collection process with each system at the same time so that different types of data generated by the different systems can be matched to a real time, universal timescale that corresponds to, for example, the anatomy of patient 113—e.g. the beating of a heart. In one example, using an NTP method, clock 126 from system 106 (MediGuide) could be used as the reference, Stratum 0 clock, while clock 122 from system 102 (X-ray) could be used as a Stratum 1 clock that is directly synchronized to the Stratum 0 clock, and clock 124 from system 104 (EnSite) could be used as a Stratum 2 clock synchronized over a network with the Stratum 1 clock.

Data output from each system can be keyed to each other to achieve synchronized output for as long as possible before an additional resynchronization is needed to be performed. Specifically, all computers that use crystal controlled clocks will inherently have an accuracy to approximately 15 microseconds. Thus, two systems will stay nominally synchronized for the Time Input Limitation divided by the inherent computer accuracy. The Time Input Limitation for the primary example is 1700 microseconds (i.e. 17 milliseconds). Thus, 1700 divided by 15 equals approximately 113 seconds. Once synchronized, after approximately 113 seconds, system 100 may become unsynchronized to an unacceptable level. Thus, system 100 may undergo a time re-synchronization procedure by repeating step 612 after every 113 seconds.

Step 610 resolves the sampling rates, such as by comparing and improving time periods, between different systems to determine how often the clocks must be re-synchronized at step 612. Furthermore, at step 610, the integration rates of sensors for the inputs at 604 and 606 can be resolved in a manner similar to how the sampling rates were resolved. In other embodiments, radiation detection sensor 238 may be used to synchronize the clocks between the first and second systems. For example, if system 102 comprises an X-ray system, another complimentary system will be able to tell exactly when radiation is being emitted and when the associated image is generated such that medical information gathered by the complimentary system can be located on the image at the correct point in time.

After clocks 122, 124, and 126 (FIG. 1) are synchronized, other input parameters of systems 102, 104, and 106 can be considered and accounted for. For example, at step 614, the accuracy of each sensor used in each system can be evaluated to determine if artificial improvement can be made. In particular, the spatial (2D and 3D) resolution of each sensor can be considered. The sensors output can be linearly interpolated to artificially increase the resolution of one sensor to match the resolution of another sensor. For example, the high resolution of 2D x-ray image 506 can be used to increase the relatively low resolution of 3D model 504 (FIG. 5), thereby improving display of soft tissue. Conversely, the spatial information form 3D model 504 can be used to increase the perceived depth of 2D x-ray image 506 (FIG. 5). Common techniques can be used to increase sensor resolution, such as sub-pixel resolution techniques and superresolution techniques.

At step 616, the native coordinate systems for systems 102, 104, and 106 are co-registered into a combined, universal coordinate system so that images and models generated by the various systems can be displayed in a single or combined view. For example, co-registering of the coordinate systems allows position sensor 120 to be placed accurately within model 504, and electrodes 118A and 118B to be accurately placed in image 506. Co-registering techniques that can be used with the present systems and methods are described in U.S. Pub. No. 2012/0265054 A1 to Olson and U.S. Pub. No. 2008/0221425 A1 to Olson et al., both of which are hereby incorporated by reference in their entirety for all purposes.

At step 618, supplemental data, such as any artifacts or additional information, is synergized with the combined data from systems 102, 104, and 106. Artifacts may comprise any structural components that are desired to be displayed with model 504 and/or image 506. In particular, the locations of position sensor 120 and electrodes 118A and 118B are known in their native coordinate systems. The location of another component relative to a known component (position sensor 120 or electrodes 118A and 118B) can be determined using either a) the other coordinate systems, or b) calculating the approximate location of the other component from the known location. For example, with reference to FIG. 5, the location of the shaft of catheter 121 can be generated in model 504 based on a) the location of catheter 121 in image 506 [e.g. using the system 102 coordinate system co-registered with the system 104 coordinate system], or b) the location of electrodes 118A and 118B [e.g. using only the system 104 coordinate system] and rendering the catheter shaft therefrom. Thus, the shaft of catheter 121 can be shown in image 506 moving with the heart using the sampling rate of position sensor 120, despite electrodes 118A and 118B not having accuracy and a sampling rate that matches that of image 506 and magnetic position sensor 120.

At step 608, information synergized by system 100 and the methods described herein are displayed for viewing by a user of system 100. For example, the data is shown on image panel 502 of display 500. As such, the user is able to rapidly visualize, assimilate and evaluate presented information.

Although the disclosure has been written with reference to particular medical systems. Almost any type of medical system can be used with the methods and systems described herein. For example, electrophysiological recording systems, cardiac stimulators, optical coherence tomography systems, pressure measurement systems, ultrasound systems, and the like may be combined and synergized into a single system and output. For example, additional information, such as cardiac stimulus feedback, can be displayed directly on model 504 or image 506. Specifically, cardiac stimulus feedback from a cardiac stimulator may be shown on display 500 either as separate ECG information, such as ECG information 510, or as wave fronts directly on model 504 as the model is shown beating. One example of a cardiac stimulator suitable for combining and synergizing according to the present disclosure is described in U.S. Pub. No. 2005/0131473 A1 to Gordon et al., which is hereby incorporated by reference in its entirety for all purposes. One such recording system is the WorkMate™ Claris™ Recording System commercially available from St. Jude Medical, Inc.

One example of an electrophysiological recording system suitable for combining and synergizing according to the present disclosure is described in U.S. Pat. No. 8,406,875 to Levin et al., which is hereby incorporated by reference in its entirety for all purposes. One example of an optical coherence tomography system suitable for combining and synergizing according to the present disclosure is described in U.S. Pat. No. 8,478,384 to Schmitt et al., which is hereby incorporated by reference in its entirety for all purposes. In another embodiment, as discussed with reference to FIG. 7, ablation data and force data from a force-sensing, magnetic-positioning-sensor-enabled catheter can be combined into an x-ray image.

FIG. 7 is an exemplary display screen 700 showing force-sensing catheter 702 being synergized with ablation data 704 in fluoroscopic image 706. Force-sensing catheter 702 includes shaft 708, ablation tip 710, and position electrodes 712. Ablation data 704 includes force icon 714, force graphical data 716, and ablation icon 718. Fluoroscopic image 706 shows interior surface 720, exterior surface 722, and back wall 724 of tissue 726, such as a heart wall.

Image 706 may comprise an X-ray image as may be generated using system 102 of FIG. 1 or moving imager 118 of FIG. 2. As such, image 706 may show a plane view with an accurate representation of heart wall 718, but in which it may be difficult to decipher the depth of wall 718, such as to back wall 724.

Ablation tip 710 may include a MediGuide enabled sensor, such as sensor 226 of FIG. 2, as is described in the aforementioned U.S. Pat. No. 8,641,705 to Leo et al. As such, a medical system is able to show the position of ablation tip 710 on image 606. Electrodes 712 may comprise electrodes similar to electrodes 118A and 118B from FIG. 1 and thus may be synergized into image 706 as previously described. Similarly, the location of shaft 708 may be determined based on the location of ablation tip 710 and electrodes 712 and synergized into image 706.

Ablation tip 710 generates graphical data 716, which is described in the aforementioned patent to Leo et al. Graphical data 716 provides a temporal indication of the magnitude of the force with which ablation tip 710 is being applied against tissue 718. Icon 714 provides a visual indication of the magnitude of the force. For example, icon 714 may become darker as more force is applied and may change shape to signify orientation of ablation tip 710. Icon 714 and graphical data 716 are generated using the same system that generates the position of ablation tip 710, and therefore are displayed in real time in synchronicity with the position of ablation tip 710. Ablation icon 718 provides a visual representation of the magnitude (e.g. depth) of tissue ablated with ablation tip 710. Generation of ablation icon 718 is described in the aforementioned patent to Leo et al.

The location of electrodes 712 and the image of heart wall 718 are generated using different systems than that used to generate icon 714, graphical data 716, and ablation icon 718. One method for incorporating position information within a volumetric rendering that can be used with the present disclosure is described in U.S. Pub. No. 2012/0169712 A1 to Hill et al., which is hereby incorporated by reference in its entirety for all purposes. However, the real time rendering of electrodes 712, and heart wall 718 within display screen 700 may lead or lag the generation of icon 714, graphical data 716, and ablation icon 718 depending on the rate at which those systems gather and display the data. However, in order for a user of the information presented in icon 714, graphical data 716, and ablation icon 718 to correlate it to the position of catheter 708 and tissue 726, it should be presented contemporaneously. For example, it is beneficial for a doctor or clinician to be able to see tissue 726 move within image or image 706 at the same time icons 714 and 718 are generated. Thus, the systems and methods of the present invention are employed to synergize the display of catheter 708, ablation tip 710, tissue 726, and ablation data 704.

The systems and methods described herein allow output from disparate medical systems to be integrated into a single medical system. As has been described above, such integration is useful for visually assimilating information to better diagnose, asses, and treat various medical conditions.

Thus, the intended use of the information being combined determines how close the systems need to be synchronized. For example, consider combining information from only a MediGuide system and an Ensite system. If you are only interested to know the general region of the heart where a catheter is located, then you might not need very precise synchronization because the physician moves the catheter relatively slowly. If MediGuide system data indicates that a catheter moves instantly, but EnSite system data shows the catheter moving only after a delay of, for example two seconds, it might still be perfectly acceptable. But, if you have an automated computer algorithm that is continuously comparing the location determined by a MediGuide system to the location determined by an EnSite system in order to initialize some kind of transformation formula between the two tracking systems, then this algorithm would get completely disrupted when it detects on the MediGuide system that the catheter moved, but there is no movement on the EnSite system yet. In view of these two scenarios, the systems and methods of the present disclosure can be adjusted to accommodate different situations and the need for different Time Input Limitations and Synchronization Windows.

As an example of the above situation, if it is desirable to synchronize all systems to within one order of magnitude (approximately ten times) of accuracy with respect to the length of time of a heart phase, then all systems need to have:

an integration time smaller than $1/10$ of the heart cycle time;
a phase value accuracy better than $1/10$ of the heart cycle time;
a synchronization accuracy better than $1/10$ of the heart cycle time; and
a sample rate faster than $1/10$ of the heart cycle time or interpolation between sampling to reduce phase-value-accuracy by less than $1/10$ of the full heart cycle.

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments.

Although a number of embodiments have been described above with a certain degree of particularity, those skilled in the art could make numerous alterations to the disclosed embodiments without departing from the sprit or scope of this disclosure. For example, all joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

Any patent, publication, or other disclosure material, in whole or in part, that is said to be incorporated by referenced herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Reference throughout the specification to "various embodiments," "some embodiments," "one embodiment," or "an embodiment," or the like, means that a particular feature, structure, or characteristic described in connection with the embodiment is included in at least one embodiment. Thus, appearances of the phrases "in various embodiments," "in some embodiments," "in one embodiment," or "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

What is claimed is:

1. A method for combining and synergizing data from different medical systems, the method comprising the following:

Obtaining, by an electronic control unit (ECU) comprising a processor, from a first medical system an image disposed relative to a first coordinate system;
Obtaining, by the ECU, from a second medical system supplemental data;
synchronizing, by the ECU, first and second clocks of the first and second medical systems, respectively;
interpolating, by the ECU, an image accuracy value of the first medical system with a three dimensional accuracy value of a sensor of the second medical system;
receiving, by the ECU, the image and supplemental data by a third medical system that displays in synchronicity the supplemental data combined with the image in real-time, the third medical system including a magnetic position sensor to generate magnetic-based location data relative to a third coordinate system; and
displaying in synchronicity, by the ECU, the supplemental data combined with the image.

2. The method of claim 1, further comprising resolving, by the ECU, an integration time for the image of the first medical system with an integration time of the supplemental data from the second medical system.

3. The method of claim 1, wherein the supplemental data comprises a least one of physiological data, electrocardiogram data, imaging data and bio-mechanical data.

4. The method of claim 1, wherein the supplemental data comprises location data and wherein the second medical system comprises an impedance-based location sensor and generates supplemental data comprising impedance-based location data relative to a second coordinate system, wherein the magnetic-based location data from the third medical system is co-registered with location data from the second medical system.

5. The method of claim 4, further comprising co-registering, by the ECU, the first, second, and third coordinate systems of the first, second, and third medical systems, respectively.

6. The method of claim 4, wherein the impedance-based location data from the second medical system is used to generate, by the ECU, an artifact relative to the magnetic-based location data from the third medical system.

7. The method of claim 6, wherein the artifact comprises a representation of at least one of:
   (a) a shaft of an elongate medical device overlaid onto the image in relation to a sensor of the third medical system; and
   (b) an electrode of a catheter overlaid onto the image in relation to the sensor of the third medical system.

8. The method of claim 1, wherein the second medical system comprises at least one of:
   (a) a force-sensing catheter, wherein the supplemental data associated with the force-sensing catheter includes force-related data; and
   (b) an optics-based sensing catheter, wherein the supplemental data associated with the optics-based sensing catheter includes blood pressure data.

9. The method of claim 1, wherein synchronizing the first and second clocks comprises at least one of:
   (a) using at least one of a network time protocol (NTP) synchronizing scheme, a precision time protocol (PTP) synchronizing scheme, and Cristian's algorithm; and
   (b) synchronizing time data resolution from the first and second medical systems.

10. A system for combining and synergizing data from different medical systems, the system comprising the following:
   a computing device comprising a data input interface, a data output interface, processor, and memory, the memory storing computer-readable instructions that, when executed by the processor, cause the processor to execute the following processes:
      obtain from a first medical system an image disposed in a first coordinate system through the data input interface;
      obtain from a second medical system supplemental data through the data input interface;
      obtain location data from the second medical system, the location data being relative to a second coordinate system from an impedance-based location sensor, and transmit data to the data output interface for displaying location sensor information in synchronicity with the image;
      obtain location data from a third medical system, the location data being relative to a third coordinate system from a magnetic position sensor, and transmit data to the data output interface for displaying position sensor information in synchronicity with the image;
      use an image accuracy value of a first sensor of the first medical system with a three dimensional accuracy value of a second sensor of the second medical system;
      synchronize first and second clocks of the first and second medical systems, respectively; and
      transmit data to the data output interface for displaying in synchronicity the supplemental data combined with the image.

11. The system of claim 10 wherein the instructions further cause the processor to execute the following process:
   use an integration time for the image of the first medical system with an integration time of the supplemental data from the second medical system.

12. The system of claim 11 wherein the instructions further cause the processor to execute the following process:
   co-register the first, second, and third coordinate systems of the first, second, and third medical systems, respectively; and
   generate an artifact in the image relative to location data from the first, second and, third coordinate systems.

13. A system for synergizing data from different medical systems, the system comprising the following:
   a first medical device configured to generate medical information correlated to a first time scale; and
   a medical positioning system comprising the following:
      a catheter configured to generate position data of a sensor relative to a magnetic coordinate system and a second time scale, wherein the magnetic coordinate system comprises a magnetic position sensor;
      circuitry configured to receive the position data, the medical information, and imaging data from an imager relative to an optical coordinate system and a third time scale, and further configured to synchronize the first, second, and third time scales and use two-dimensional spatial accuracy of the imaging data from a first sensor with three-dimensional spatial accuracy of the position data; and
      a display unit configured to display real-time, time-synchronized imaging data, location data, and medical information.

14. The system of claim 13 wherein the circuitry is further configured to use at least one of:
   (a) sensor integration times of the first medical device, the catheter, and the imager.

15. The system of claim 13, wherein the first medical device comprises an x-ray imaging system, and the medical positioning system further comprises a radiation detection sensor, wherein the circuitry is configured to determine when the first medical device is activated using the radiation detection sensor in order to synchronize the medical information with the position data.

16. The method of claim 1, wherein the image accuracy value of the first medical system is used to adjust the three dimensional accuracy value of the sensor of the second medical system.

* * * * *